US012678378B2

(12) United States Patent (10) Patent No.: US 12,678,378 B2
Gruber et al. (45) Date of Patent: Jul. 14, 2026

(54) REMINERALIZING DENTAL MATERIAL

(71) Applicant: Muhlbauer Technology GmbH, Hamburg (DE)

(72) Inventors: Dominik Gruber, Constance (DE); Stephan Neffgen, Pinneberg (DE); Olav-Sven Becker, Scheggerott (DE); Holger Muller, Pinneberg (DE); Helmut Colfen, Constance (DE); Elena Sturm, Constance (DE)

(73) Assignee: Muhlbauer Technology GmbH, Hamburg (DE)

( * ) Notice: Subject to any disclaimer, the term of this patent is extended or adjusted under 35 U.S.C. 154(b) by 1214 days.

(21) Appl. No.: 17/602,162

(22) PCT Filed: Apr. 8, 2020

(86) PCT No.: PCT/EP2020/000081
§ 371 (c)(1),
(2) Date: Oct. 7, 2021

(87) PCT Pub. No.: WO2020/207618
PCT Pub. Date: Oct. 15, 2020

(65) Prior Publication Data
US 2022/0202655 A1 Jun. 30, 2022

(30) Foreign Application Priority Data
Apr. 8, 2019 (DE) .......................... 102019109150.0

(51) Int. Cl.
| | |
|---|---|
| *A61K 6/20* | (2020.01) |
| *A61K 6/69* | (2020.01) |
| *A61K 6/70* | (2020.01) |
| *A61K 6/80* | (2020.01) |
| *A61K 8/81* | (2006.01) |
| *A61Q 11/00* | (2006.01) |

(52) U.S. Cl.
CPC .................. *A61K 6/20* (2020.01); *A61K 6/69* (2020.01); *A61K 6/70* (2020.01); *A61K 6/80* (2020.01); *A61K 8/8147* (2013.01); *A61Q 11/00* (2013.01)

(58) Field of Classification Search
CPC ... A61K 6/20; A61K 6/70; A61K 6/69; A61K 6/80; A61K 8/8147; A61Q 11/00
See application file for complete search history.

(56) References Cited

U.S. PATENT DOCUMENTS

| | | | | |
|---|---|---|---|---|
| 5,820,853 | A | * 10/1998 | Glandorf | ............... A61Q 11/00 424/57 |
| 5,885,552 | A | * 3/1999 | Causton | ................. A61K 8/733 424/48 |

| | | | |
|---|---|---|---|
| 2007/0183984 | A1 | 8/2007 | Haas et al. |
| 2010/0272764 | A1 | 10/2010 | Latta et al. |
| 2010/0305626 | A1 | 12/2010 | Stewart et al. |
| 2014/0193777 | A1 | 7/2014 | Rusin et al. |
| 2014/0242005 | A1 | 8/2014 | Koumans |
| 2016/0058675 | A1 | 3/2016 | Xu et al. |
| 2019/0054012 | A1 | 2/2019 | De Pablo et al. |

FOREIGN PATENT DOCUMENTS

| | | | |
|---|---|---|---|
| JP | 2007-099632 A | 4/2007 | |
| JP | 2011-510152 | 3/2011 | |
| JP | 2013-500072 | 1/2013 | |
| JP | 2014-502296 | 1/2014 | |
| WO | WO 97/06774 | 2/1997 | |
| WO | WO 2007/090242 A1 | 8/2007 | |
| WO | WO 2011/011658 A1 | 1/2011 | |
| WO | WO 2012/065148 A2 | 5/2012 | |
| WO | WO 2017/161179 | 9/2017 | |
| WO | WO-2017209823 A2 * | 12/2017 | ............. A61K 35/32 |

OTHER PUBLICATIONS

Shu-Chen Huang, Kensuke Naka, and Yoshiki Chujo, Langmuir 2007, 23, 12086-12095. (Year: 2007).*

Ackermann et al., "Biomimetic transformation of polyphosphate microparticles during restoration of damaged teeth" Dental Materials 2019, 35: 244-256.

Cantaert et al., "Think Positive: Phase Separation Enables a Positively Charged Additive to Induce Dramatic Changes in Calcium Carbonate Morphology" Adv. Funct. Mater. 2012, 22: 907-915.

Huang et al., "A Carbonate Controlled-Addition Method for Amorphous Calcium Carbonate Spheres Stabilized by Poly(acrylic acid)s" Langmuir 2007, 23: 12086-12095.

International Search Report and Written Opinion for Intl. Appl. No. PCT/EP2020/000081, mailed Jun. 22, 2020, 12 pages.

Jiao et al., "Complementarity and Uncertainty in Intrafibrillar Mineralization of Collagen" Adv. Funct. Mater. 2016, pp. 1-18.

Kim et al., "Functional biomimetic analogs help remineralize apatite-depleted demineralized resin-infiltrated dentin via a bottom-up approach" Acta Biomaterialia 2010, 6: 2740-2750.

Shellis, Etiology and Pathogenesis of Caries, Caries Management—Science and Clinical Practice, 2012, pp. 25-26.

Shellis, Etiology and Pathogenesis of Caries, Caries Management—Science and Clinical Practice, 2012, p. 23.

Twetmann, K.R. Ekstrand, Caries Management by Influencing Mineralization, Caries Management-Science and Clinical Practice, 2013, p. 190.

* cited by examiner

*Primary Examiner* — Michael P Cohen

(74) *Attorney, Agent, or Firm* — Casimir Jones, S.C.; Anne M. Reynolds

(57) ABSTRACT

A subject of the invention is a remineralizing dental material, having at least one cation and at least one anion, which are configured as partner ions for forming a remineralization substance. In accordance with the invention at least one of the partner ions is multivalent and is included as counterion in a coacervate. A further subject of the invention is a kit for producing such a dental material, and also the use thereof.

30 Claims, 6 Drawing Sheets

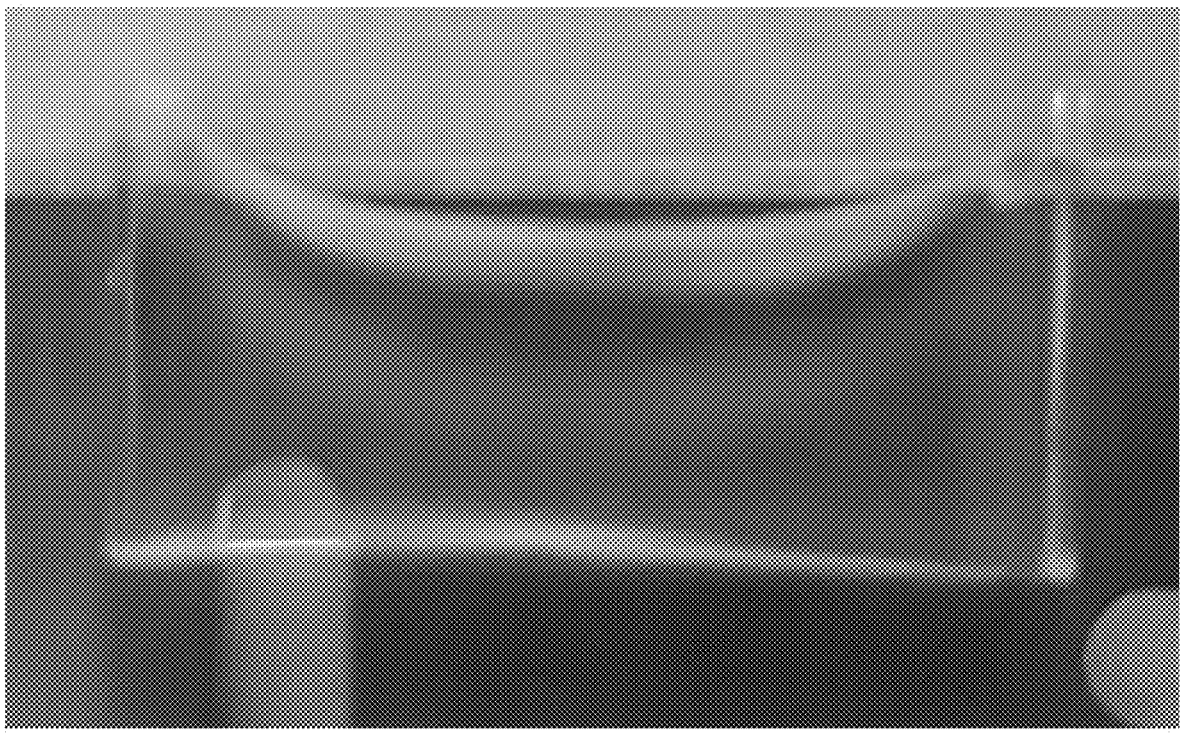
Fig. 1: Photograph of the depth mineralization in cross section for example 11 after 12 d. Visible below the concave cut edge of the gel body is a mineralized region (milky white). Evident below it at some distance is a further region of mineral material (pale grey).

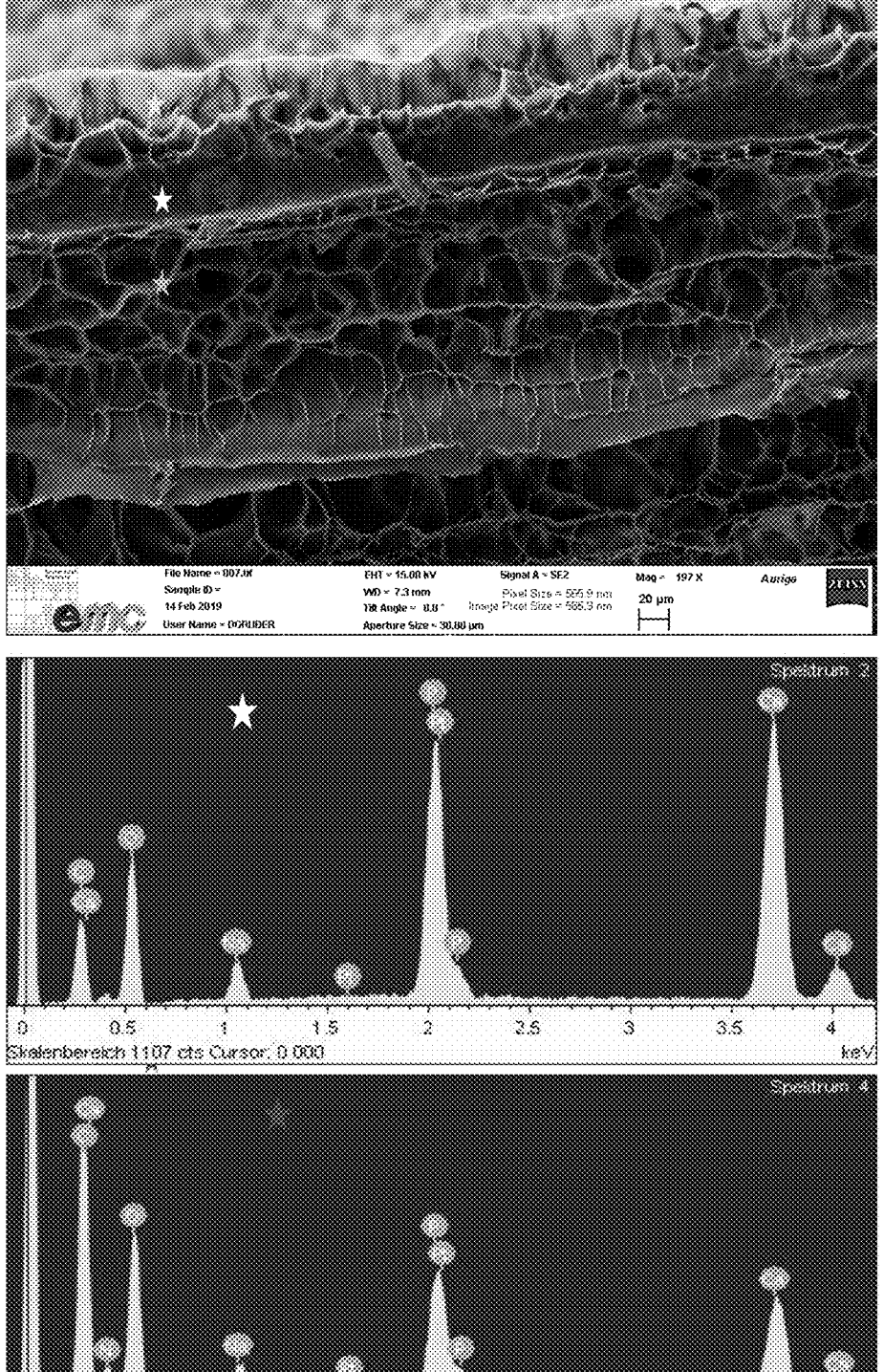
Fig. 2: SEM/EDX of the mineral formed in the gelatin in example 11 after 12 d (cross section)
[Skalenbereich = scale range]

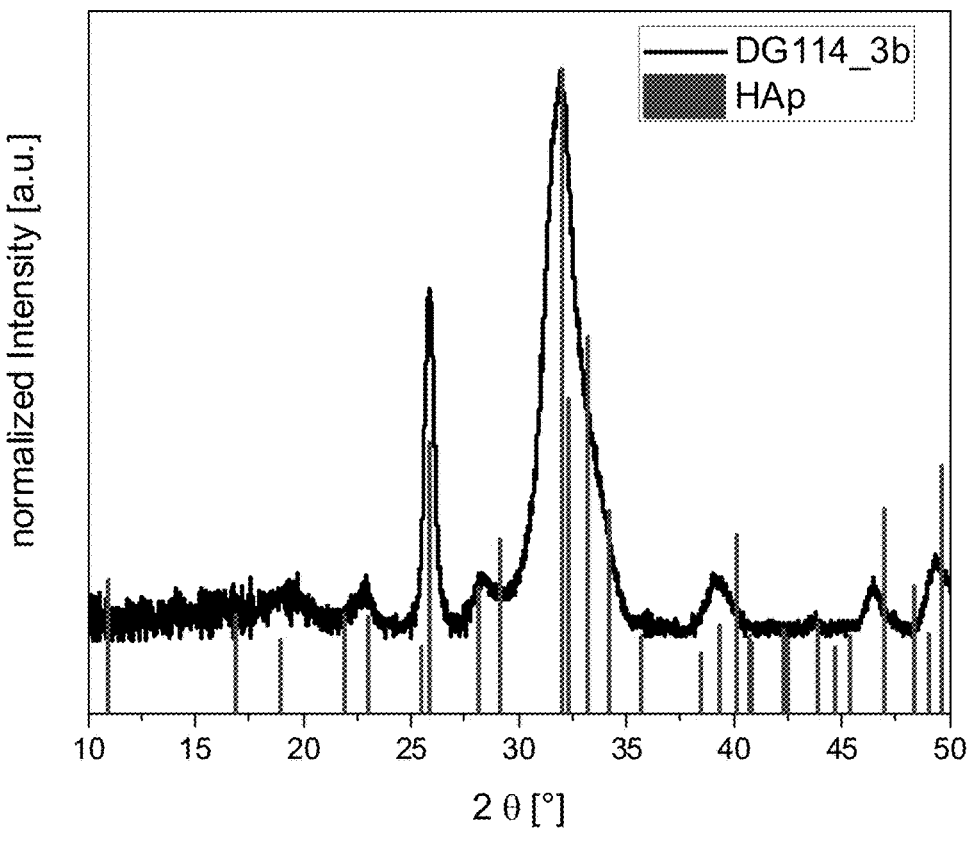
Fig. 3: XRD of the mineral formed in example 11 after 12 d
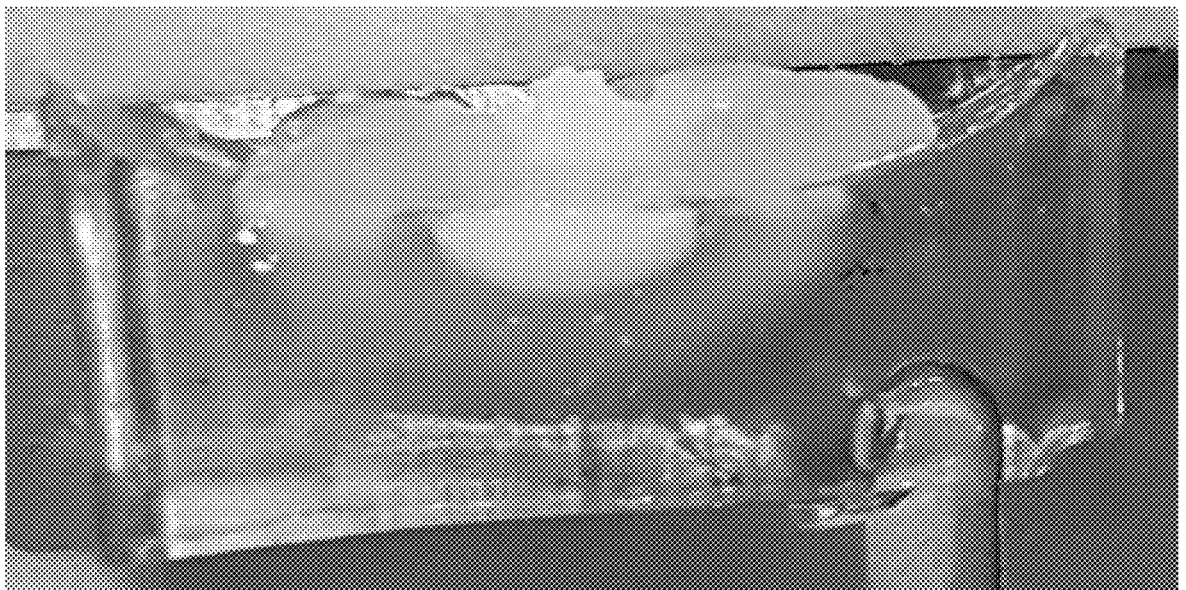
Fig. 4: Photograph of the depth mineralization in cross section for example 12 after 3 d

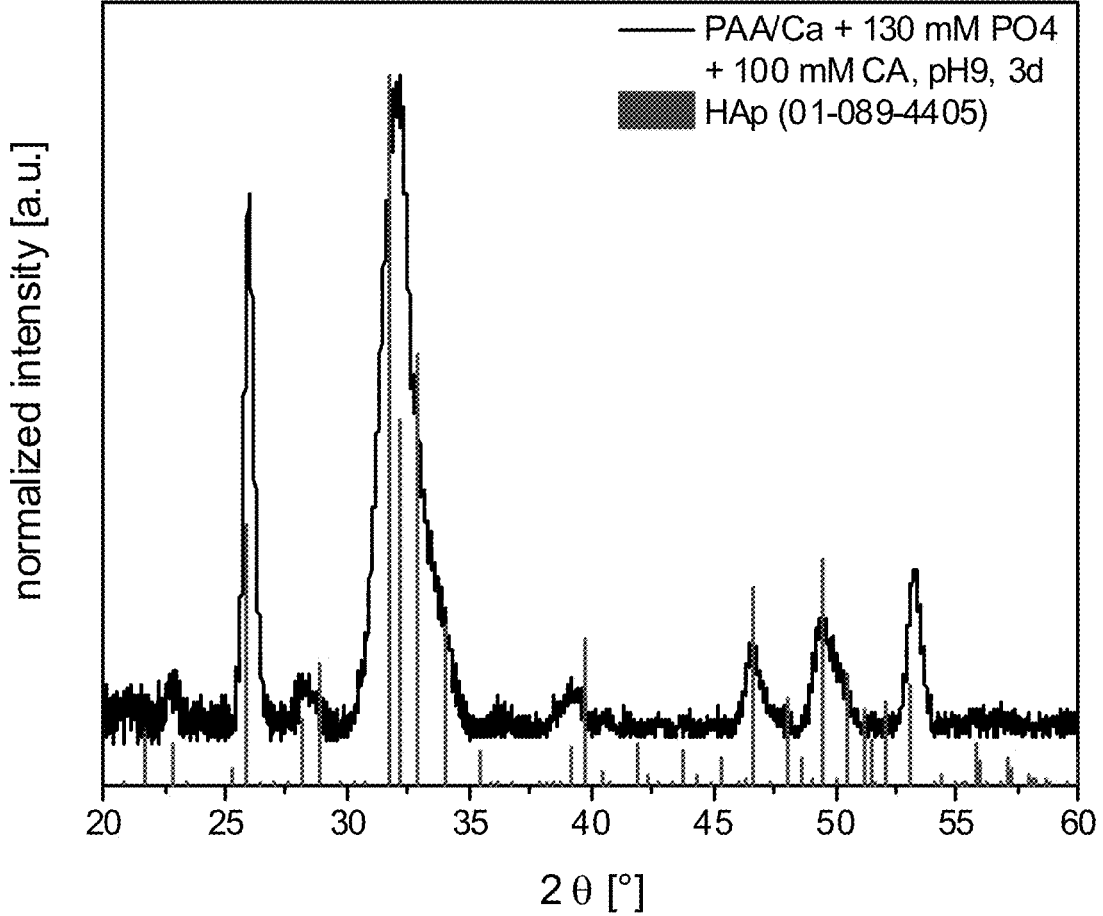
Fig. 5: XRD of the mineral formed in example 12 after 3 d

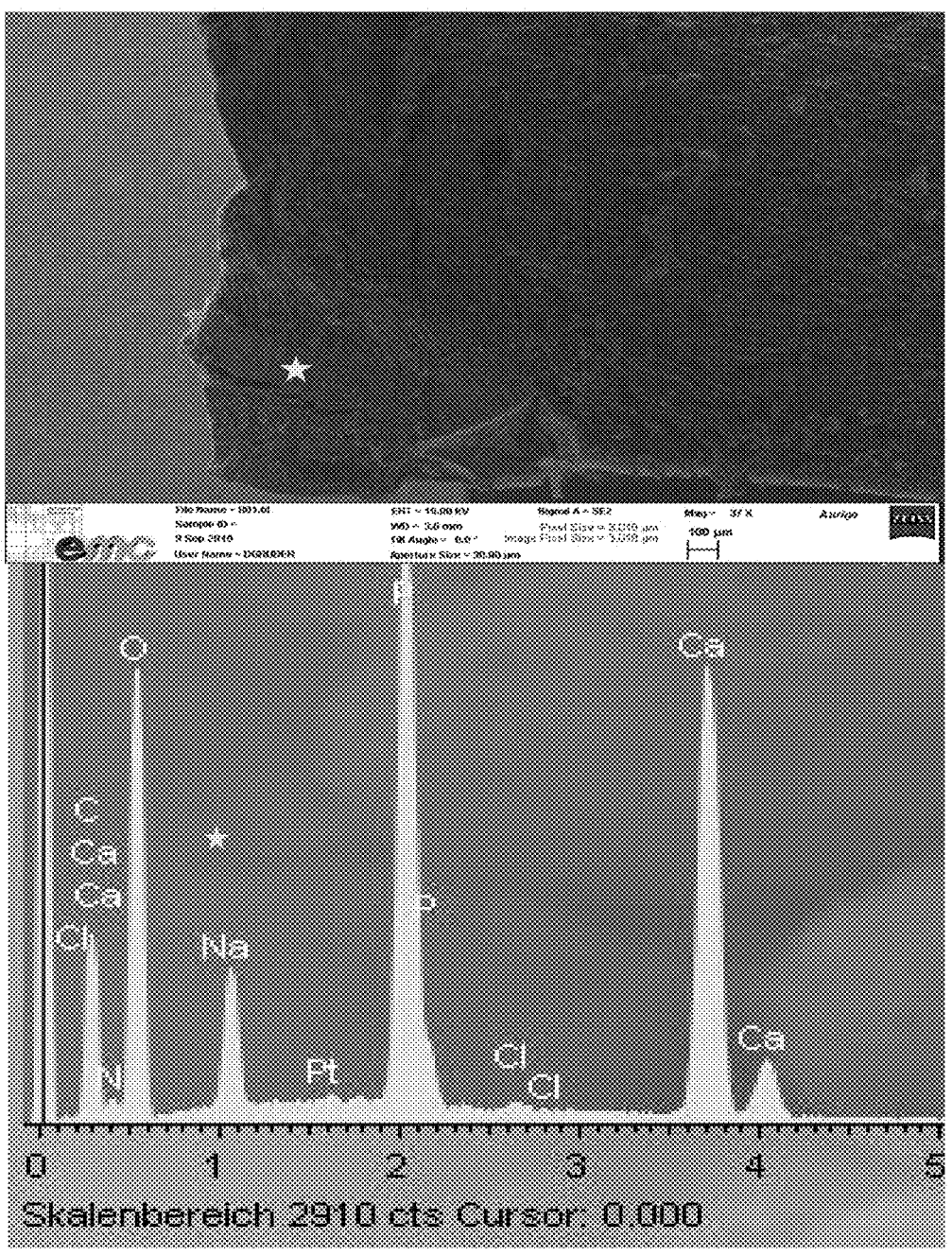
Fig. 6: SEM/EDX of the mineral formed in the gelatin in example 12 after 3 d (cross section).
[Skalenbereich = scale range]

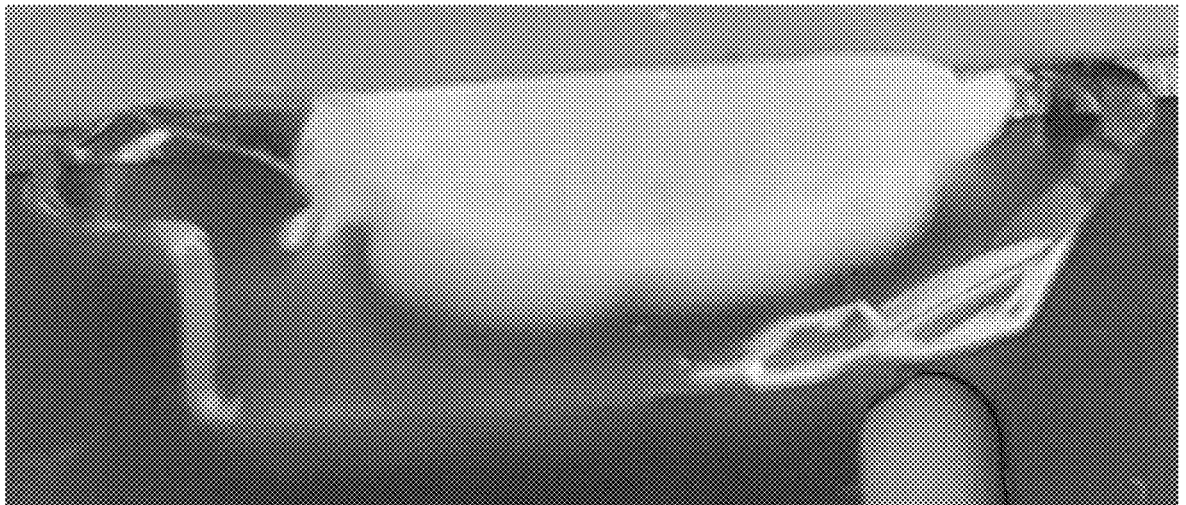
Fig. 7: Photograph of the depth mineralization in cross section for example 13 after 2 d

REMINERALIZING DENTAL MATERIAL

The invention relates to a remineralizing dental material, having at least one cation and at least one anion, which are configured as partner ions for forming a remineralization substance. A further subject of the invention is the use of this dental material, a method for use thereof, and a kit for producing it.

Dental materials for all kinds of conservative treatment of defects in dental hard substance are known. Through a mineralizing effect of such materials, the aim is to stabilize the natural dental hard substance, remaining after an invasive treatment, for example, against further degradation— that is induced by bacteria, for example. Mineralization in this case may be induced by release of certain ions such as $Ca2^+$ or $F^-$ from the material, with entry of suitable counterions from the saliva on or in the dental hard tissue. Then new inorganic solid material of low solubility is formed, and replaces lost mineral in the dental hard substance (mineral replacement). Other approaches are aimed at the formation of mineral solids, primarily hydroxyl apatite or other apatites, without the need for entry of $Ca^+$ or phosphate ions from the saliva. Here, in the prior art, the primary use is of what are called bioactive glasses.

The mineralization potential of materials based on the prior art is generally limited. The reasons for this are on the one hand a limited amount of available, i.e., partially soluble suitable ions in the material in question (e.g., glass ionomer cements), and on the other hand that in the classes of material in question, because of the nature of the material, the use of only limited amounts of ion sources (e.g., composites with bioactive glasses) in conjunction with acceptable physical properties is possible. The amount of the ions released and/or of the mineral replacement formed is limited from such materials, and consequently cannot be sufficient for sustained stabilization of the dental hard substance.

WO2017/161179A1 discloses a remineralizing composition which comprises a 60:40 mixture of Bioglass 45S5 and polyaspartic acid. It yields only a low concentration of releasable ions. Moreover, there are limits on the selection and combination possibilities of releasable ions, and hence on the nature of the remineralization.

US2010/0272764A1 discloses a polymerizable dental resin composite with remineralizing capacities. This composite comprises microcapsules each containing a calcium nitrate solution, a potassium hydrogen phosphate solution, and a sodium fluoride solution. The ions are released through the semipermeable membrane of the capsules by way of a concentration gradient. The microcapsules are said to be producible by complex coacervation of oppositely charged polyelectrolytes. A disadvantage here as well is the low concentration of releasable ions.

The object on which the invention is based is that of creating a dental material of the abovementioned kind that enables effective remineralization.

In order to achieve this object, the invention proposes that at least one of the partner ions is multivalent and is included as counterion in a coacervate.

To start with, an explanation will be given of certain terms used in the context of the invention.

The invention relates to a remineralizing dental material.

Remineralization and demineralization are biological processes which take place in alternation in the interface between the tooth and the oral cavity, and in which mineral ions are either dissolved out or incorporated again via the saliva. Demineralization refers to the generally acid-induced (owing to cariogenic plaque, for example) loss of mineral by the tooth owing to the dissolution of the inorganic, primarily hydroxyl apatite-containing constituents of the tooth, which represents a primary process in the formation of caries (P. Shellis in: Karies [Caries], H. Meyer-Lückel, S. Paris, K. R. Ekstrand eds., G. Thieme Verlag, 2012, p. 23).

Remineralization in the narrower sense encompasses the accretion or depletion of mineralike material, based primarily on apatite, in the region of the tooth surface (P. Shellis, loc. sit., pp. 23, 26; S. Twetmann, K. R. Ekstrand, loc. sit., p. 210). In the case of a dental substance damaged beforehand by demineralization, a remineralization process of this kind leads to a certain repair of the defects. The replacement material may accrete on existing apatite crystals of the tooth and lead to crystal growth, although new apatite crystals may also be formed. According to the current status of research, it is assumed that the natural remineralization process is promoted in the presence even of low concentrations of fluoride.

Remineralization in the sense of the present invention refers to any process in which inorganic material is accreted onto the existing dental hard substance, potentially damaged by demineralization, through processes of precipitation. This precipitation may bring about the growth of existing apatite crystals in the dental substance, or else may lead to the formation of new inorganic material at the remineralization site. Suitable inorganic materials may be materials derived from apatite, or else may be other biocompatible compounds of low solubility. They are referred to in the invention as remineralization substance.

Dental substance refers to any mineralized tooth substance, especially enamel, dentin, and tooth cement.

Partner ions are cations and anions which are able together to form a remineralization substance.

Coacervation is a term for a liquid-liquid phase separation. An ionic polymer or macroion (e.g., an ionic polyphosphate), together with a multivalent counterion (e.g., calcium), forms a coacervate which forms a relatively polymer-rich phase within the polymeric solution.

Coacervates are polyelectrolytes crosslinked via multivalent counterions. In an aqueous medium, coacervates take the form of a phase of higher viscosity. Depending on the height of the molecular weights of the parent polyelectrolytes, the coacervates take the form of liquid, viscous to viscoplastic substances, present in phase-separated form in the aqueous medium. Coacervates exist only within a certain range of the amount-of-substance ratio between polyelectrolyte and multivalent counterion, and also only beyond a certain minimum concentration of the polyelectrolyte. If the counterion fraction is too low or if the concentration of the coacervate formers (multivalent counterion and polyelectrolyte) is too low, there is no phase separation in water.

Suitable coacervates are formed from anionic or cationic polyelectrolytes and multivalent cations or multivalent anions. Suitable coacervates contain ionic polyelectrolyte and multivalent counterions that crosslink this polyelectrolyte.

The coacervates are produced preferably by mixing the aqueous solutions of anionic or cationic polyelectrolytes and of multivalent cations or anions. In this context, anionic polyelectrolytes and multivalent cations are mixed, and cationic polyelectrolytes and multivalent anions are mixed.

The coacervates form a separate liquid phase of higher viscosity in the mixture. The coacervates are preferably isolated. This is accomplished in each case by suitable known methods such as decanting or centrifuging. The isolated coacervates are preferably purified. This is accomplished preferably by simple washing with a solvent, preferably with water.

The invention has recognized that partner ions of a remineralization material having a high mineralization potential for dental hard substance can be made available in a dental material if at least one of these partner ions is present as counterion in a coacervate. Through a mineralizing effect, the aim is to stabilize the natural dental hard substance, remaining after an invasive treatment, for example, against further degradation—that is induced by bacteria, for example. Mineralization in this case may be induced by release of certain ions such as $Ca^{2+}$ or $F^-$ from the material, with entry of suitable partner ions from the saliva on or in the dental hard tissue. Then new inorganic solid material of low solubility is formed, and replaces lost mineral in the dental hard substance (mineral replacement).

Conversely, the mineralization potential of known dental materials is limited. One of the reasons for this is that the known components with mineralizing effect can be added to a dental material only in limited amounts without impairing the other physical properties of said material. A further reason is the limited rate and amount in which the ions can be delivered into the corresponding dental material and/or from the dental material, in the case of known glass ionomer cements, for example.

For use, dental materials of the invention with a mineralizing effect are present advantageously in a liquid or pastelike form, but at least in an adaptable form, and are applied in this form to the dental hard substance to be treated. There they are applied manually to the surface and potentially shaped. Since remineralization processes tend to be very slow, the material ought to remain at the site of use at least for a certain time after hardening. In a use particularly suitable for long-term treatment success, the material solidifies after a certain time, and the working time must be sufficient for manual operations on the material. In that case the hardened form of the material also serves to protect the remineralization site from mechanical and/or chemical degradation. Before and, if envisaged, after the hardening, the materials ought to be capable of supplying ions for the mineralization of the dental hard substance, with formation of mineral replacement.

In one preferred use, the dental materials with mineralization potential are to be used rationally for the stabilization of enamel. This may be enamel partially degraded by carious processes, enamel in the region of exposure to invasive dental treatments, or regions undermineralized as a result of misformations in the enamel (e.g., MIH). A desirable dental material mineralizes the undermineralized dental hard substance in contact and covers such regions at least for a period which is needed for the mineralization of the enamel regions. Also conceivable is a permanent dwelling in the sense of a filling material. Use leads to stabilization of the tooth substance, encompassing the remineralization and the physical protection over the period which is needed for remineralization. In such a use, the material in question ideally also bonds at the location to be treated.

A further desirable specific use of mineralizing dental materials is aimed at stabilizing existing or remaining dentin. Such applications are directed, for example, at exposed dentin in the region of exposed tooth necks. It is known that this clinical situation in particular is difficult to manage, because durable and impervious sealing in this region is very difficult. This is especially so in the therapy of tooth neck caries, which is difficult to treat clinically. In this use as well, the material has both a physically protecting effect and a mineralizing effect, and acts in this way for stabilization. Here again, for clinical reasons, the material is to be able to be secured adhesively on the dentin in the step of use itself.

Another preferred use of such materials is directed at their utility as relining material, especially when deep cavities are present and in certain circumstances demineralized dentin remains in the cavity. Here again, stabilizing effects and a durable protection are the aim. A problem with the materials in the prior art is that relinings based on inorganic materials do not always have sufficient chemical stability and/or do not bond, or bond only inadequately, to the substrate.

A preferred requirement of the mineral replacement formed is that in chemical terms it is at least as stable to an acidic aqueous environment as the dental hard substance (hydroxyl apatite), and more preferably it is more stable. Stability against acidic aqueous environment refers to the resistance to dissolution in such a medium. Formation of such chemically stable mineral replacements prevents the material dissolving in the face, for example, of microbiological exposure and formation of acid.

In the invention it is preferable that one of the partner ions is multivalent and is included as counterion in a coacervate, and a second partner ion is included in aqueous solution.

With this embodiment there may preferably be a second polyelectrolyte additionally included, having a different charge from the polyelectrolyte of the coacervate. If, then, the polyelectrolyte of the coacervate is a cationic polyelectrolyte, this second polyelectrolyte is an anionic polyelectrolyte, and vice versa. It has emerged that the addition of such a second polyelectrolyte means that there is additional depth mineralization into the dental substance (more particularly dentin). This has the advantage, especially in the case of demineralized dentin, that the mineralization potential can be improved via the depth of penetration of a partner ion included in the coacervate, allowing improved remineralization into the depth of the dentin.

In the invention both partner ions may be multivalent and included as counterion of a respective coacervate. More preferably one of the partner ions is divalent, i.e. the charge is 2. Preferred charge numbers are +3, +2, −2 and −3.

As well as multivalent cations/anions, coacervates may also include univalent cations/anions. It may be preferable for fractions of the multivalent or else univalent cations to possess antimicrobial properties. Suitable cations having these properties are, for example, silver ions or copper ions. It may be preferable for fractions of the multivalent or else univalent anions to have biological effects or else remineralization-supporting effects. It is particularly preferable for fluoride to be included as univalent anion.

The anionic polyelectrolytes for forming the coacervates with multivalent cations may preferably be selected from the group of the organic polyelectrolytes, preferably consisting of polymers and copolymers which contain carboxylic acid groups, phosphoric acid groups, phosphonic acid groups and/or sulfonic acid groups, and also their salts and their partial esters; preferably polycarboxylic acids, polyalkylene phosphoric acids, polyalkylene phosphonic acids, for example polyvinyl phosphonic acid and polysulfonic acids, and also their salts and their partial esters; more preferably poly(meth)acrylic acid, polyaspartic acid, polyitaconic acid, and polyglutamic acid, and also their salts;

acidic proteins, acidic protein derivatives, and their salts, preferably of lysozyme or of gelatin (type B);

acidic polysaccharides and their salts, preferably of carrageenan, of pectin, of algic acid, and of hyaluronic acid.

The anionic polyelectrolytes for forming the coacervates with multivalent cations preferably have average molecular weights (weight average Mw) of between 3 kDa and 1500 kDa, more preferably between 5 and 500 kDa, more preferably between 8 kDa and 200 kDa, more preferably still between 8 and 50 kDa.

The multivalent cations are preferably selected from the group consisting of mineral-forming cations; preferably metal cations; more preferably the metals of groups 2A, 3B, and 3A of the PTE and also the lanthanoids; more preferably $Ba^{2+}$, $Ca^{2+}$, $Sr^{2+}$, $Tb^{3+}$, and $Yb^{3+}$; more preferably $Ca^{2+}$ and/or mixtures of metal cations with $Ca^{2+}$.

Coacervates with cation mixtures, e.g., by partial substitution of $Ca^{2+}$ by—in particular—$Sr^{2+}$ in Ca-containing coacervates, are possible.

In one preferred embodiment of a coacervate based on polyacrylic acid and $Ca^{2+}$ ions, for forming the desired isolatable coacervate, at least a pH of 5 and a polyacrylic acid concentration of ≥1 mg/ml, more preferably ≥10 mg/ml, are provided.

The cationic polyelectrolytes for forming the coacervates with multivalent anions are preferably selected from organic polyelectrolytes, preferably from the group consisting of polymers and copolymers which contain primary, secondary and/or tertiary amino groups, and also their salts; preferably polyamines; more preferably polyallylamine, linear or branched polyethyleneimine, chitosan, polylycine, and polyarginine and also their salts; more preferably polyallylamine hydrochloride (PAH).

One embodiment of coacervate based on cationic polyelectrolytes may be the combination of polyallylamine hydrochloride (PAH) with phosphate or hydrogen phosphate as counterion. In this embodiment it should be ensured that for producing the coacervate, the polyallylamine is present in as far as possible protonated form and the phosphate ion in as far as possible deprotonated form.

The cationic polyelectrolytes for forming the coacervates with multivalent anions preferably have average molecular weights (weight average Mw) of between 3 kDa and 1500 kDa, preferably between 5 and 500 kDa, more preferably between 8 kDa and 200 kDa, more preferably still between 8 and 50 kDa.

The multivalent anions are preferably selected from the group consisting of mineral-forming anions, preferably orthophosphate ions, diphosphate ions, metaphosphate ions, silicate ions, more particularly inorganic silicate ions, preferably ortho, ino, and band gap silicate ions, and partially organically modified silicate ions, more particularly alkyloxy-silicate ions, sulfate ions, tungstate ions, vanadate ions, molybdate ions, and carbonate ions, more preferably orthophosphate ions, diphosphate ions, metaphosphate ions, sulfate ions, tungstate ions, vanadate ions, molybdate ions, more preferably orthophosphate ions and/or mixtures of orthophosphate ions with mineral-forming anions.

The dental material of the invention is in one embodiment preferably a liquid and/or an emulsion and/or a suspension, preferably having a dynamic viscosity of greater than 50 mPas, preferably greater than 100 mPas.

The dental material of the invention is in another embodiment preferably a solid, more preferably a powder.

The dental material of the invention is in another embodiment preferably a gel or a paste.

The dental material may contain 1 to 100 wt % of partner ions and coacervate; preferred lower limits and upper limits are 5, 10, 15, 25, etc. up to 95 wt %. The stated intervals of 5 wt % in each case can be combined arbitrarily in the invention to form ranges of lower limits and upper limits.

The dental material of the invention comprises preferably water, preferably between 5 and 95 wt %; preferred lower limits and upper limits are 5, 10, 15, 25, etc. up to 95 wt %. The stated intervals of 5 wt % in each case can be combined arbitrarily in the invention to form ranges of lower limits and upper limits.

In the invention the coacervate in one embodiment may have a water content of 0.1 to 90 wt %, preferably 1 to 75 wt %, more preferably 5 to 60 wt %.

In a preferred embodiment, after drying, for example, the coacervate may have a water content of 0.1 to 50 wt %, preferably 1 to 25 wt %, more preferably 5 to 25 wt %.

In the invention it is preferable for the concentration of the polyelectrolyte forming the coacervates, and its counterions, in the coacervate to be between 10 and 100 wt %; preferred lower limits are 25 or 40, more preferably 45 wt %; preferred upper limits are 55 or 75, more preferably 85, 90, and 95 wt %.

In the invention it is preferable for fluoride ions to be included as partner ion.

In the invention it is preferable for the partner ions in the dental material to be present substantially in soluble form (especially before formation of the remineralization substance).

The dental material of the invention may be self-curing in configuration.

In the invention it is preferable for the dental material to have a working time and/or hardening time of between 1 and 5 min according to ISO 9917:2007.

In the invention it is preferable for the cured dental material to be self-bonding, preferably having a shear bond strength of at least 3.5 MPa on enamel and/or dentin.

The cured dental material preferably has a compressive strength of greater than 50, preferably greater than 100, more preferably greater than 200 MPa and a flexural strength of greater than 20, preferably greater than 25 MPa according to ISO 9917:2007.

The dental material of the invention has a high mineralization potential for the dental hard substance and, in a particularly preferred form, forms a mineral replacement which has a solubility in acidic media of pH 4.2, that is below the solubility of hydroxyl apatite.

The dental material may in the invention comprise additives, such as pigments, dyes, antioxidants, preservatives, fillers or other consistency agents, which may be added, for example, for adjusting the rheology. For improving the mechanical properties it is possible for inert inorganic or organic fillers, such as silicates, glasses, $ZrO_2$, $BaSO_4$, $SiO_2$, and prepolymers, to be admixed to the dental material. Fillers able to actively influence the mineralization may also be used. Cited here illustratively are ion-releasing glasses such as ionomer glasses and bioactive glasses, hydroxyl apatite particles, amorphous calcium phosphate (ACP) or tetracalcium phosphate (TCP). Hydroxyl apatite, more particularly in the form of nanoparticles having an average particle diameter of 5-100 nm, is particularly preferred. Furthermore, by adding water-soluble particles of partner ions of the invention, especially salts of calcium, of phosphate, and of fluoride, more particularly $CaCl_2$ particles and $(NH_4)_2HPO_4$ particles, it is possible to achieve a further increase in the mineral content and the ion reservoir for these species. Water-soluble citrates are another preferred additive. For coloration it is possible to add inorganic or organic color pigments. These pigments may serve to adapt the color of the material to the dental hard substance, or else to introduce a contrast between material and tooth.

As further possible additives it is possible to introduce monomers, e.g., (meth)acrylates, or double bond-containing polyelectrolytes into the system. Through the additional possibility of curing the polyelectrolyte system by a second curing mechanism, the properties of the dental material described may be additionally influenced. Depending on architecture, the polymerizable monomer units may be crosslinked with the polyelectrolytes. Partial functionalization of the coacervates used is also possible.

In the invention, the term "aqueous solution" also covers those solutions which contain water in homogeneous solution with, for example, organic solvents. Such solutions contain preferably more than 10 wt % of water, more preferably more than 50 wt % of water, and with particular preference the sole solvent is water.

Polyelectrolytes may be understood in particular as being polymers which carry charged groups attached directly or via spacer groups to the polymer chain. These charged groups may be either negatively charged groups or positively charged groups. It is preferable for charges of one sign only to be located on each polymer chain. The number of charged groups per polymer chain here may vary within wide ranges. For example, the polymer chain of a suitable polyelectrolyte may comprise not only monomer units which carry charge carriers but also monomer units without charge carriers. A suitable polyelectrolyte preferably possesses a solubility of more than 1 mg ml$^{-1}$.

Coacervates are produced in general by exchanging the counterions of dissolved polyions for those which form coacervates with the polyion. A production step of this kind is achieved simply by mixing the polyions, in solution in water, with the corresponding coacervate-forming counterions in solution in water. The resultant coacervates are subsequently freed from excess residual ions by simple washing operations, and can be isolated as bodies varying from syruplike through to highly viscous or viscoelastic. In a simple example, the sodium salt of polyacrylic acid is admixed with $CaCl_2$. Beyond a certain concentration of the $Ca^{2+}$ ions in the solution, and a corresponding ratio of $Ca^{2+}$/carboxylate, phase separation occurs, and a liquid, hydrous coacervate can be isolated. Coacervates can be employed in liquid form in a continuous/macroscopic phase. A characteristic of the coacervates of the invention is the variable water content. From the coacervate phase separated from the solution, water can be removed until—for example—a solid is obtained. This water removal is reversible. The coacervates may then be used preferably in ground form as powders. The powders are produced preferably by drying and subsequent grinding of the dried coacervates. Drying takes place at temperatures below 250° C., preferably below 100° C., 60° C. under standard pressure, 40° C. under reduced pressure, for example, or preferably by freeze-drying. Grinding is possible with a multiplicity of the techniques described in the prior art, dry or wet, in suitable liquid media. A further possibility is that of use in the form of suspensions or emulsions. Powder, suspension or emulsion may be referred to collectively below using the term "finely divided forms".

For the sake of simplicity, a coacervate based on anionic polyelectrolytes is referred to below as coacervate a), and a coacervate based on cationic polyelectrolytes as coacervate b).

Where a coacervate is contacted with an aqueous solution of an ion (partner ion) which is capable of forming a compound of low solubility in water with the crosslinking counterion of the coacervate, there is a slow precipitation of the compound of low solubility at the interface with the coacervate.

In one embodiment the hydrous coacervate is based on polyacrylic acid and $Ca^{2+}$ ions. In this embodiment, phosphate may be used as partner ion. For the mineralization, in this form, a solution containing $(NH_4)_2HPO_4$ in a concentration of 10 mM to 250 mM, preferably 130 mM, has proven advantageous. The pH in this embodiment likewise has a critical influence on the formation of mineral replacement. During the mineralization, the pH drops without the use of additional buffers. The use of a buffer, such as TRIS, for example, may be beneficial for properties of the dental material.

In another embodiment the hydrous coacervate is based on polyallylamine phosphate ions. In this case, $Ca^{2+}$ ions may be used as partner ions. For the mineralization, solutions containing $CaCl_2$ in a concentration of 10 mM to 250 mM, more preferably 130 mM, have proven advantageous. In this embodiment as well, the pH has a critical influence on the formation of mineral replacement.

In one embodiment the tooth surface is contacted over a certain period with a solution containing the partner ion. The coacervate is then applied to this surface and adapted areally (e.g., as a film), where it remains until sufficient mineralization of the tooth substance has taken place. An optional possibility is to apply another type of coacervate to this treated surface.

In this form of use, the coacervate may on the one hand be applied as a viscous liquid. On the side facing away from the tooth, the arrangement may then be protected for the desired period, so that there is no premature loss of the coacervate layer. In another form of use, the coacervate may be applied in finely divided form to the tooth surface treated with the partner ion. In this case its use as a powder is also possible, since in the oral environment there is always a sufficient amount of water present which is necessary for mineralization processes.

In another embodiment the coacervate is mixed in finely divided form with the solution of the partner ion and is applied in this form to the tooth surface to be treated. Here again, mineral replacement is formed starting from the interfaces of the coacervate particles, which are also able to act on the tooth substance.

The combination of coacervates based on oppositely charged polyelectrolytes leads, firstly, to the formation of highly crosslinked and solid interpolymer complexes of these polyelectrolytes, these complexes being insoluble in water. Secondly, given a suitable choice of counterions, mineral replacement comes about. That is, the material undergoes solidification, forming inorganic solids, whose precursors are part of the starting components in the form of coacervates.

In principle, components comprising the coacervates a) and b) may be mixed with one another as liquid components, isolated in substance, which then very rapidly form solids. It may be more advantageous to use finely divided coacervates, which are mixed in the presence of water on use. The working time and hardening time of such coacervate combinations may each be controlled through the choice of the particle or particulate size distribution. Another possibility is to apply coacervates in layers one after another.

In one preferred embodiment the finely divided components comprising coacervates a) and b) are mixed in the presence of aqueous solutions and applied to the tooth substance to be treated. There they undergo solidification primarily as a result of the formation of the insoluble interpolymer complexes. As the reaction progresses further, the mineral replacement-forming ions are released from coacervates, and the mineral replacement is formed in the region of exposure to the coacervate mixtures and also in the region of the dental hard substance.

In one form of use, in which dried, pulverized components comprising coacervates a) and b) are mixed with one another, it is necessary to admix water or aqueous solutions before use on the tooth substance, in order to enable the reaction. The admixing of water or aqueous solutions takes place preferably before use on the tooth substance, by means, for example, of mixing-in by hand or automatic methods such as mixing by capsule.

Powder and water or aqueous solution are mixed preferably in a weight ratio between 5:1 to 1:50, preferably between 2:1 to 1:10, and more preferably between 2:1 to 1:2. In one preferred embodiment the coacervates a) and b) are mixed as powders in a weight ratio (sum total of a) and b)) to water or aqueous solution between 2:1 to 1:10, preferably between 2:1 to 1:1, and more preferably of 3:2.

It is also possible to apply the individual powders or the powder mixture to a moist tooth surface, where the reactions take place as stated above.

One preferred aspect of these mixed pulverized coacervates is a mixture of Ca-polyacrylic acid coacervate with a polyallylamine-phosphate coacervate. In the case of this mixed coacervate, a mass ratio of 1:1 is advantageous. Mass ratios from 5:3 up to 3:5 are also possible. The amount of water, optionally to be admixed, is guided by the target mixing consistency which is needed in the particular use.

In another embodiment a nonaqueous dispersion of a mixture of the dried powders of the components with coacervates a) and b) in a completely water-miscible solvent (e.g., glycerol) is mixed before use with a further aqueous component. The mixture is then applied to the tooth substance to be treated, where hardening and mineralization processes take place.

It may be preferable for aqueous emulsions of the components containing coacervates a) and b) in each case, optionally containing further soluble, mineral replacement-forming salts in the aqueous phase, to be mixed with one another before use. This mixture is applied to the tooth substance to be treated, where again hardening and mineralization processes take place.

An aqueous emulsion of a coacervate or plurality of coacervates as dental material contains at least 1 percent by weight, preferably at least 2 percent by weight, more preferably at least 5 percent by weight of coacervate.

Mixing may be performed in each case by hand or by using automatic mixing methods, as for example by deploying the two-component material from dual cartridges and mixing by way of a static or dynamic mixer.

In order to obtain early bonding between tooth surface and dental material, in one preferred use, before the application of the components of the coacervates a) and b) mixed with one another, the dental hard substance to be treated is treated with an aqueous solution of a polyacid or a polybase or of salts thereof. It is particularly preferable for the surface of the tooth substance to be treated with a polyacid and then for the mixture of a) and b) to be applied. In a further use, the aqueous solution of a polyacid is first applied to the tooth substance, and then the aqueous solution of the polybase, before lastly the mixture of a) and b) is applied. The use of a polyacid or a polybase as described herein before the application of the dental material of the invention is to be differentiated from the likewise inventive addition of such a polyacid or polybase to the dental material of the invention itself.

On account of its mineral replacement-forming and mineralizing properties, over the course of time, the dental material of the invention develops a more intense interaction with the dental hard substance and so counteracts a destabilizing effect on the bonding as a result of exposures to the environment. Such interaction may involve, for example, the construction of mineral replacement bridges between dental material and dental hard substance.

Since the amounts of mobile ions in coacervates are comparatively large, the mineralization potential of the coacervates for the dental hard substance is correspondingly high. Through the choice of the combination of the counterions in the coacervate it is also possible to influence the nature of the mineral replacement and therefore its chemical stability.

A further subject of the invention is a kit for producing a remineralizing dental material of the invention, which comprises the following constituents:

a first component which comprises at least one coacervate with one of the partner ions as counterion of the coacervate;

a second component, which comprises water;

wherein the second of the partner ions is included either as free ion in aqueous solution in the second component and/or as counterion of a second coacervate in one of the two components.

Preferably at least one of the components is a solid, more preferably a powder.

In another preferred embodiment, at least one of the components is a liquid, preferably having a dynamic viscosity at 23° C. of greater than 10 mPas, more preferably greater than 50 mPas, very preferably greater than 100 mPas.

In another preferred embodiment at least two of the components are pastes.

In another preferred embodiment at least two of the components are a gel.

In the invention it is preferable for at least one of the components, preferably at least two of the components, to have a pH of 7 to 9 at 23° C.

The kit preferably comprises a further component c, which preferably has a pH of less than 7 and comprises an adhesion promoter. The adhesion promoter is preferably a polyacid or a polyamine which is protonated, preferably to an extent of at least 10%. The use described here of a polyacid or a polyamine before the application of the dental material of the invention is to be differentiated from the likewise inventive addition of these materials to the dental material of the invention itself. In the invention it is likewise possible for such a component to have a dual function, as adhesion promoter on the one hand and constituent of the dental material itself on the other hand.

Preferably components a and b are stored in an apparatus suitable for mixing, preferably in a mixing capsule, containing preferably a powder and/or a liquid, and/or in a multi-compartment cartridge, as part of a cartridge system for extruding the components through a mixing needle, comprising preferably two pastes or two gels.

In one preferred embodiment, one of the partner ions is multivalent and is included as counterion in a coacervate; a second partner ion is included in aqueous solution. At least one of the components further comprises a second polyelectrolyte, which has a different charge from the polyelectrolyte of the coacervate.

In the invention it is preferable for component a to comprise at least one coacervate a) or b) and to comprise at least one polyelectrolyte which has a different charge from the polyelectrolyte of the coacervate and is not present in the form of coacervate.

In the invention it is preferable for component a to comprise at least one coacervate powder containing multivalent anions as counterions, and at least one powder of an anionic polyelectrolyte.

In the invention it is preferable for component a to comprise at least one coacervate powder containing multivalent cations as counterions, and at least one powder of a cationic polyelectrolyte.

In the invention it is preferable for component a to comprise at least one first coacervate powder comprising alkaline earth metal ions, preferably calcium ions, as counterions, and at least one second coacervate powder comprising multivalent anions as partner ions.

A further subject of the invention is a method for using a kit of the invention, with the steps of:
    i. applying constituent b to dentin and/or enamel, preferably as liquid
    ii. applying constituent a to the dentin with constituent b and/or to the enamel with constituent b, preferably as powder, paste, gel or viscous liquid.

Likewise a subject of the invention is a method for using a kit of the invention, with the steps of:
    i. mixing constituent a and constituent b,
    ii. applying the mixture to dentin and/or enamel, preferably as paste or gel.

A further subject of the invention is the use of the dental material of the invention as sealant, coating, as relining material and/or filling material, as luting cement, for pulp capping, as bone cement, as dental lacquer, as fissure sealant, as desensitizer, as remineralization agent in the prophylaxis or treatment of carious lesions; or for producing such materials.

Working examples of the invention are elucidated below.

Methods

Loss on Drying

The freshly synthesized coacervates were weighed out and then stored in a vacuum drying cabinet (Thermo Scientific Heraeus VT6025) at 40° C. and 50 mbar in each case for at least 24 h. The loss on drying was calculated from the initial weighed mass and the final weight.

Thermogravimetry (TGA)

The thermogravimetric analysis (TGA) was carried out in air from 25° C. to 1000° C. with a heating rate of 10 K/min (STA 449FS Jupiter, Netzsch).

The parameter evaluated was the loss in mass to 250° C., which was ascribed to the residual water content (freeze-dried powders).

Energy-Dispersive x-Ray Spectroscopy (EDX)

Contents of elements were determined using the following instruments: SEM/EDX; TM 3000 Tabletop SEM, Hitachi, and Quantax EDX detector, Bruker). The freeze-dried powders were used.

Compressive Strength

The test specimens were produced using a two-part mold made from stainless steel which has six cylindrical holes with a height of $4\pm0.02$ mm and a diameter of $2\pm0.01$ mm. The mold was placed on a glass plate and the dental material was introduced into the holes. When the holes were filled up with material, the openings of the holes were scraped off flat. The specimens were stored in the mold at 37° C. and around 100% relative humidity for 1 h. Subsequently the specimens together with mold were taken from the humidity chamber. The mold was opened, the specimens, with a height of around 4 mm and a diameter of around 2 mm, were removed, and the compressive strength was measured using a universal testing machine from Zwick (model Z 010/TN2A) (compressive strength after 1 h). To determine the compressive strength after 4 d, the demolded test specimens were stored again at 37° C. and at 100% atmospheric humidity in a humidity chamber for 4 d. The specimens were then taken from the chamber and the compressive strength was measured using a universal testing machine from Zwick:
    constant advancement speed: 1.0 mm/min
    the compressive strength (CS) is calculated according to the following formula: $CS\ [MPa]=F/(n\ r^2)$
    where
    F is the maximum force exerted on the specimen, in newtons;
    r is the radius of the specimen in millimeters.

Measurement was carried out in each case for six specimens, and the mean was determined from the six measurement values.

Shear Bond Strength

In order to determine the shear bond strength (SBS), bovine incisors without pulp were embedded in a cold-polymerizing resin (Viscovoss GTS with MEKP MEH hardener; Voss Chemie). Immediately before use, the embedded teeth were sanded down wet to the enamel or dentin (P120 sandpaper) and then reground wet with a fine sandpaper (P500). Prior to being used, the teeth were stored in demineralized water. For measurement, the teeth were taken from the demineralized water. Then a two-part Teflon mold with a hole of 3.0 mm in diameter (ISO/TS 11405:2003) was placed on, and was secured with a metal bracket, and the cavity was filled with the dental material. After filling of the cavity, Hostaphan film was placed on and a glass slide was placed on and secured with a further metal bracket. The filled molds were stored in the humidity chamber at 37° C. for 4 d, after which demolding took place. The test specimens were then subjected to measurement with a shearing apparatus according to ISO10477:2004 and in an apparatus for the determination of a force-distance diagram (Z010/TN2A, Zwick GmbH & Co., Ulm, Germany) with a rate of advance of 0.5 mm/min. The testing was carried out on three specimens in each case.

Dynamic Viscosity

The viscosity was measured at 23° C. by means of a dynamic plate/plate viscometer (Dynamic Stress Rheometer, Rheometric Scientific Inc.). Measurement took place in the Steady Stress Sweep mode with gap sizes of 0.1 to 0.5 mm in the range from 0 to 50 Pa shear stress.

Mineralization/x-Ray Diffractometry (XRD)

The dental material from example 6 was cured in a thin layer. The material was then stored in the humidity chamber at 37° C. for 5 d. The dried material was mortared and analyzed in this form by x-ray diffractometry (Bruker D8, Discover).

From coacervates a) and partner ions in aqueous solution (examples 9, 10)

After the end of the mineralization time, the mixture was centrifuged, decanted, and washed three times with 1.75 of ultrapure water. The washed centrifugation residues were then dried at 37° C.

The dried products were investigated by x-ray diffractometry (XRD), as powders in each case, for their mineral phases. For examples 11 and 12, mineralized material was removed from the interior of the gel body, and analyzed in this form by x-ray diffractometry (Bruker D8, Discover).

Particle Size Determination

For the determination of the particle size distribution, 250 mg of the freeze-dried and ground coacervates were dispersed in 20 ml of ethanol for 5 min in an ultrasound bath. The particle size was measured subsequently using a particle size analyzer by means of Fraunhofer diffraction (Laser Diffraction Particle Size Analyzer LS 13 320 with Universal Liquid Module, Beckmann Coulter) in adulterated ethanol.

Chemicals used were as follows:

Polyacrylic acid sodium salt solution (NaPAA15, Mw=15 kDa), 35 wt. % solution (Sigma Aldrich)

Polyacrylic acid (PAA100, Mw=100 kDa), 35 wt. % solution (Sigma Aldrich)

Polyallylamine hydrochloride (PAH15, Mw=15 kDa), 15 wt % solution (Polyscience)

Polyallylamine hydrochloride powder (Mw=17.5 kDa, Sigma)

Trisodium citrate tetrahydrate (Sigma Aldrich)

Calcium chloride dihydrate (Roth)

Diammonium hydrogen phosphate (Sigma Aldrich)

Strontium chloride (Roth)

Sodium hydroxide (Merck)

Hydrochloric acid (Merck)

Ultrapure water (MilliQ, Merck Millipore)

Gelatin (300 bloom, a type)

Synthesis of Coacervates Based on Polyacrylic Acid Salts

Examples 1-4

An aqueous polyacrylic acid sodium salt solution was admixed slowly, with vigorous stirring, with an aqueous calcium chloride solution or calcium strontium chloride solution. Phase separation was observed during the addition. Following complete addition, stirring took place for five minutes more and the phases were then left to rest for 10 minutes for further separation. The supernatant formed was poured off and the phase which remained was washed three times with 400 ml of ultrapure water in each case. A viscous liquid was obtained. The pH values were adjusted in each case using hydrochloric acid and/or sodium hydroxide solutions. The amounts, concentrations, and pH values of the solutions used are reported in table 1.

TABLE 1

Amounts, concentrations, and pH values of the solutions used for coacervate synthesis

| | Na-PAA15 solution | | | PAA100 solution | | | Alkaline earth metal salt solution | | | |
| | Conc.* | | | Conc.* | | | Conc.* | | | |
| Coacervate | PAA15 [mg/mL] | Amount [mL] | pH | PAA100 [mg/mL] | Amount [mL] | pH | CaCl$_2$ [mM] | SrCl$_2$ [mM] | Amount [mL] | pH |
|---|---|---|---|---|---|---|---|---|---|---|
| Example 1 | 100 | 60 | 9 | — | — | — | 200 | — | 200 | 6 |
| Example 2 | — | — | — | 100 | 60 | 9 | 200 | — | 200 | 6 |
| Example 3 | 100 | 60 | 9 | — | — | — | 125 | — | 200 | 6 |
| Example 4 | 100 | 60 | 9 | — | — | — | 150 | 50 | 200 | 6 |

*Conc. = concentration

Synthesis of Coacervate Based on Polyallylamine Hydrochloride

Example 5

An aqueous polyallylamine hydrochloride solution was admixed slowly, with vigorous stirring, with an aqueous (NH$_4$)$_2$HPO$_4$ solution. Phase separation was observed during the addition. Following complete addition, stirring took place for five minutes more and the phases were then centrifuged at 7700 g for 3 minutes for further separation. The supernatant formed was poured off and the phase which remained was washed three times with 10 ml of ultrapure water in each case. A viscous liquid was obtained.

The pH values were adjusted in each case using hydrochloric acid and/or sodium hydroxide solutions. The amounts, concentrations, and pH values of the solutions used are reported in table 2.

TABLE 2

Amounts, concentrations, and pH values of the solutions used for coacervate synthesis

| | PAH15 solution | | | (NH$_4$)$_2$HPO$_4$ solution | | |
| | Conc.* [mg/mL] | Amount | | Conc.* [mM] | Amount | |
| Coacervate | PAH15 | [mL] | pH | (NH$_4$)$_2$HPO$_4$ | [mL] | pH |
|---|---|---|---|---|---|---|
| Example 5 | 10 | 15 | 3 | 200 | 10 | 7 |

*Conc. = concentration

Water Content/Loss on Drying of the Viscous Liquids Obtained in Examples 1, 4 and 5

The water contents of the viscous liquids were determined by loss on drying. The loss on drying is reported as water content in table 3a.

TABLE 3a

Loss on drying/water contents of the coacervates

| Coacervate | Water content [% by weight] |
|---|---|
| Example 1 | 55 |
| Example 4 | 55 |
| Example 5 | 35 |

Ion Content of Freeze-Dried Samples of the Viscous Liquid Obtained in Examples 1, 4 and 5

The ion content was determined as element content by means of energy-dispersive x-ray spectroscopy (EDX). The residual water content of the freeze-dried viscous gels was determined by thermogravimetry (TGA). Residual water contents and element contents are reported in table 3b.

TABLE 3b

Residual water content determined by TGA and element contents determined by EDX for freeze-dried coacervates

| | Coacervate | | | |
| | Residual water [% by weight] | Calcium [% by weight] | Strontium [% by weight] | Phosphorus [% by weight] |
|---|---|---|---|---|
| Example 1 | 8 | 20 (20[a]) | — | — |
| Example 4 | 8 | 14 | 8 | — |
| Example 5 | 8 | — | — | 17 |

[a]TGA value

Production of Coacervate Powders
Coacervate Powder (P1)

Water was removed from the viscous liquid from example 1 by freeze drying. The resulting material was ground in a vibratory mill (Pulverisette 0, from Fritsch) for 7 h, then in a mortar mill (Pulverisette 2, from Fritsch) for 6 h, and lastly in a ball mill (ball distribution: 55×16 mm, 14×25 mm, 4×40 mm) for 18 h.

The residual water content of the white powder obtained was determined by TGA. The residual water content was 8% by weight. Particle size distribution: $D_{10}=1.0$ µm and $D_{50}=4.4$ µm Coacervate Powder (P2)

Water was removed from the viscous liquid from example 5 by freeze drying. The resulting material was ground in a vibratory mill (Pulverisette 0, from Fritsch) for 7 h, then in a capsule mixer (1 ml; ball diameter: 3.15 mm; Silamat, from Ivoclar-Vivadent) for 60 s, and lastly in a capsule mixer (1 ml; ball diameter: 0.1 mm; Silamat, from Ivoclar-Vivadent) for 60 s. The residual water content of the white powder obtained was determined by TGA. The residual water content was 8% by weight. Particle size distribution: $D_{10}=2.4$ µm and $D_{50}=24.6$ µm Polyallylamine Hydrochloride Powder (P3)

This powder is a second, cationic polyelectrolyte, which in accordance with the invention can be used together with a coacervate containing anionic polyelectrolyte and which promotes depth mineralization in the manner already referred to above and illustrated in the examples.

Example 6

Production of a Self-Adhesive, Self-Curing Dental Material from Coacervate Powders P1 and P2

To produce the dental material, 150 mg of powder P1 were mixed with 150 mg of powder P2. This powder mixture and also 0.2 ml of water were introduced separately from one another into a mixing capsule (Applicap, DMG Hamburg).

The powder and the liquid were mixed using a vibratory mixer (Silamat, Ivoclar Vivadent AG) for 20 s to give a ready-to-use treatment material.

Immediately after mixing, the resulting treatment material was delivered from the mixing capsule via the needle of the mixing capsule, and was processed.

Example 7

Production of a Self-Adhesive, Self-Curing Dental Material from Coacervate Powder P1

300 mg of powder P1 and 0.2 ml of $(NH_4)_2HPO_4$ solution (130 mM, pH 9) were mixed manually with the aid of a spatula on a tray for around 30 s to form a ready-to-use treatment material.

Example 8

Production of a Self-Adhesive, Self-Curing Dental Material from Coacervate Powder P1

300 mg of the ground powder P1 and 0.2 ml of a 130 mM $(NH_4)_2HPO_4$ and 100 mM sodium citrate solution, adjusted to a pH of 9, were mixed by manual mixing for around 30 s to form a ready-to-use treatment material. In comparison with example 7, this material cures much more quickly.

Example 9

40 mg of the ground powder P1 and 1.75 ml of a 130 mM $(NH_4)_2HPO_4$ solution, adjusted to a pH of 9, were mixed manually by means of a spatula for around 30 s in a 2 ml reaction vessel (Eppendorf tube), briefly shaken and then stored horizontally at room temperature for 5 min and 24 h, respectively.

Example 10

40 mg of coacervate powder P1 were mixed with 1.75 ml of an aqueous solution containing 130 mM $(NH_4)_2HPO_4$ and 100 nM sodium citrate (in analogy to example 8) in a 2 ml reaction vessel (Eppendorf tube), briefly shaken and then stored horizontally at room temperature for 5 min and 24 h, respectively.

Characterization

The Compressive Strength was Determined for the Dental materials of examples 6-8. The compressive strengths are reported in table 4.

TABLE 4

Compressive strengths of the dental materials

| | Compressive strength after 1 h [MPa] | Compressive strength after 4 d [MPa] |
|---|---|---|
| Example 6 | 4.6 ± 1.2 | 21.2 ± 1.4 |
| Example 7 | 12.6 ± 1.3 | 32.3 ± 3.1 |
| Example 8 | 7.5 ± 2.1 | 9.3 ± 3.1 |

The compressive strength was highest for the material of example 7. For all of the dental materials the compressive strengths were higher after 4 days than 1 h after processing.

Shear Bond Strength (SBS)

The shear bond strength was measured for examples 6-8. The dental material is self-adhesive. In the specimens, cracking or deformation of the specimens occurred before they were sheared off.

Mineralization

The mineralization of the mixtures of examples 6, 9 and 10 was investigated by means of XRD. The mineral phases detected are reported in table 5.

17

18

TABLE 5

| Detected mineral phases | | |
| --- | --- | --- |
| Mineral phases after 5 d | Mineral phases after 5 min | Mineral phases after 24 h |
| Example 6 | HAP, OCP, DCPD | — | — |
| Example 9 | — | HAP | HAP |
| Example 10 | — | HAP | HAP |

Use Examples

Production of Model Substance

For the use examples below, model substances for demineralized dentin were first produced. Each model substance consists of a gel which is solid at room temperature.

At 40° C., 10 g of gelatin (A type, 300 bloom) were dissolved in 90 ml of an aqueous solution having a pH of 9, containing 130 mM diammonium hydrogen phosphate and 100 mM trisodium citrate tetrahydrate. The resulting gelatin solution was introduced into standard 24-well titer plates and allowed to cool to room temperature. As soon as room temperature was reached, the solid gel bodies were removed from the titer plate using a spatula and were stored in the aqueous solution.

Application of Dental Materials to the Model Substances

The dental materials were applied in each case to the surface of the model substance, i.e., to the top sides of the disk-shaped gel bodies, and were stored at room temperature in 10 ml of the aqueous solution (containing 130 mM diammonium hydrogen phosphate and 100 mM trisodium citrate tetrahydrate, pH 9) such that the dental material and the model substance were covered by the solution, or they were stored in a conditioning cabinet at 100% atmospheric humidity and room temperature. After 2 d, 3 d, 4 d, 8 d or 12 d, the gel bodies were removed and washed with ultrapure water. Then, using a razor blade, cross sections of the disk-shaped gel body were prepared. The cross sections were examined optically to ascertain whether mineralized material was evident under the model substance surface, and how deep this material reached into the model substance.

Examples 11 to 13

In the same way as for example 6, self-adhesive, self-curing dental materials were produced. The powders/powder mixtures and liquids used in this case are illustrated in table 6 below.

| Example | Powder P1 [mg] | Powder P3 [mg] | Aqueous solution [ml] | $HPO_4^{2-}$ content of aqueous solution [mM] | Citrate content of aqueous solution [mM] |
| --- | --- | --- | --- | --- | --- |
| 11 | 150 | 0 | 0.1 | 130 | 100 |
| 12, 13 | 150 | 50 | 0.13 | 130 | 100 |

The liquid constituent used is the aqueous solution containing $(NH_4)_2HPO_4$ and sodium citrate, as already used in example 8 also.

In examples 12 and 13, the powder mixture contains powder P3 as second, cationic polyelectrolyte, which is used together with the coacervate containing anionic polyelectrolyte (powder P1) and which promotes depth mineralization in the manner already mentioned above.

To produce the dental material, 150 mg of the respective powder/powder mixture and also the liquid constituent were introduced separately from one another into a mixing capsule (Applicap, DMG Hamburg). The powder and the liquid were mixed using a vibratory mixer (Silamat, Ivoclar Vivadent AG) for 20 s to form a ready-to-use treatment material. Immediately after mixing, the resulting treatment material was delivered from the mixing capsule via the needle of the mixing capsule, and processed.

The dental materials thus produced were applied to model substance, and the mineralization tested, in accordance with the use examples below.

Example 11

The dental material from table 6 above, example 11, was applied to the model substance and stored as described in the aqueous solution.

After 4 d, a slight depth mineralization was apparent. After 12 days, the depth mineralization observed was still only slight (FIG. 1). For the mineral formed in the gelatin, calcium, carbon, phosphorus, and oxygen were detected over the entire depth (FIG. 2). The mineral was identified by XRD as hydroxyl apatite (FIG. 3).

Example 12

The dental material from table 6 above, example 12, was applied to the model substance and stored as described in the aqueous solution.

After just 3 d, substantial depth mineralization is observed (FIG. 4). The dental material applied to the gelatin surface bonds to the surface, is stable, and does not break down. The mineral formed may be identified by XRD measurements as hydroxyl apatite (FIG. 5). For the mineral formed in the gelatin, calcium, carbon, phosphorus, and oxygen can be detected by EDX analyses (FIG. 6).

Example 13

The dental material from table 6 above, example 13, was applied to the model substance and stored as described in the conditioning chamber.

After just 2 d, pronounced depth mineralization was apparent (FIG. 7). The dental material bonds to the surface, is stable, and does not break down. The mineral formed was identified by XRD as hydroxyl apatite.

What is claimed is:

1. A kit for producing a remineralizing dental material, wherein the remineralizing dental material has at least one cation and at least one anion, which are configured as partner ions for forming a remineralization substance, wherein at least one of the partner ions is multivalent and is included as counterion with a polyelectrolyte in a coacervate, the kit comprising the following constituents:

a. a first component which comprises at least one coacervate with one of the partner ions as counterion of the coacervate;

b. a second component comprising water;

wherein the second of the partner ions is included either as free ion in aqueous solution in component b and/or as counterion of a second coacervate in one of the two components.

2. The kit as claimed in claim 1, wherein at least one of the components has a pH of 7 to 10 at 23° C.

3. The kit as claimed in claim 1, wherein components a and b are stored in an apparatus suitable for mixing.

4. The kit as claimed in claim 1, wherein component a comprises at least one first coacervate powder comprising calcium ions as counterions, and at least one second coacervate powder comprising multivalent anions as partner ions.

5. The kit as claimed in claim 1, wherein at least one of the components is a solid.

6. The kit as claimed in claim 5, wherein at least one of the components is a powder.

7. The kit as claimed in claim 1, wherein at least one of the components is a liquid.

8. The kit as claimed in claim 7, wherein the liquid has a dynamic viscosity of greater than 100 mPas.

9. The kit as claimed in claim 1, wherein the two components are pastes.

10. The kit as claimed in claim 1, wherein the two components are gels.

11. The kit as claimed in claim 1, which comprises a further component c, which comprises an adhesion promoter.

12. The kit as claimed in claim 11, wherein the polyelectrolyte is an organic polyelectrolyte selected from the group consisting of:
   a. polymers and copolymers which contain carboxylic acid groups, phosphoric acid groups, phosphonic acid groups and/or sulfonic acid groups, and also their salts and their partial esters;
   b. acidic proteins, acidic protein derivatives, and their salts; and
   c. acidic polysaccharides selected from carrageenan, pectin, algic acid, and hyaluronic acid, and their salts.

13. The kit as claimed in claim 12, wherein the organic polyelectrolyte is selected from the group consisting of polycarboxylic acids, polyalkylene phosphoric acids, polyalkylene phosphonic acids, and polysulfonic acids, and also their salts and their partial esters.

14. The kit as claimed in claim 13, wherein the organic polelectrolyte is selected from the group consisting of poly(meth)acrylic acid, polyaspartic acid, polyitaconic acid, and polyglutamic acid, and also their salts.

15. The kit as claimed in claim 12, wherein the organic polyelectrolyte is selected from lysozyme and gelatin.

16. The kit as claimed in claim 12, wherein the organic polyelectrolyte is selected from carrageenan, pectin, alginic acid, and hyaluronic acid, and their salts.

17. The kit as claimed in claim 1, wherein one of the partner ions is multivalent and is included as counterion in a coacervate, and a second partner ion is included in aqueous solution, with at least one of the components further comprising a second polyelectrolyte, which has a different charge from the polyelectrolyte of the coacervate.

18. The kit as claimed in claim 1, wherein the polyelectrolyte is an anionic polyelectrolyte for forming the coacervates with multivalent cations, and the anionic polyelectrolyte is selected from the group consisting of organic polyelectrolytes.

19. The kit as claimed in claim 18, wherein the multivalent cations are selected from the group consisting of mineral-forming cations.

20. The kit as claimed in claim 19, wherein the multivalent cations are selected from the group consisting of $Ba^{2+}$, $Ca^{2+}$, $Sr^{2+}$, $Tb^{3+}$, and $Yb^{3+}$.

21. The kit as claimed in claim 20, wherein the multivalent cations are $Ca^{2+}$ and/or mixtures of metal cations with $Ca^{2+}$.

22. The kit as claimed in claim 1, wherein the polyelectrolyte is a cationic polyelectrolyte for forming the coacervates with multivalent anions, and the cationic polyelectrolyte is selected from organic polyelectrolytes.

23. The kit as claimed in claim 22, wherein the organic polyelectrolyte is selected from the group consisting of polyallylamine, linear or branched polyethyleneimine, chitosan, polylysine, and polyarginine and also their salts.

24. The kit as claimed in claim 23, wherein the organic polyelectrolyte is polyallylamine hydrochloride (PAH).

25. The kit as claimed in claim 22, wherein the multivalent anions are selected from the group consisting of mineral-forming anions.

26. The kit as claimed in claim 25, wherein the multivalent anions are selected from the group consisting of orthophosphate ions, diphosphate ions, metaphosphate ions, silicate ions, sulfate ions, tungstate ions, vanadate ions, molybdate ions, and carbonate ions.

27. The kit as claimed in claim 26, wherein the multivalent anions are orthophosphate ions and/or mixtures of orthophosphate ions with mineral-forming anions.

28. A method for using a kit as claimed in claim 1, with the steps of:
   i. applying constituent b to dentin and/or enamel,
   ii. applying constituent a to the dentin with constituent b and/or to the enamel with constituent b.

29. A method for using a kit as claimed in claim 1, with the steps of:
   i. mixing constituent a and constituent b,
   ii. applying the mixture to dentin and/or enamel.

30. The method as claimed in claim 28, comprising applying constituent b to dentin and/or enamel as a liquid.

* * * * *